US006991910B2

(12) United States Patent
Adorante et al.

(10) Patent No.: US 6,991,910 B2
(45) Date of Patent: Jan. 31, 2006

(54) HIGH-THROUGHPUT SCREEN FOR IDENTIFYING CHANNEL BLOCKERS THAT SELECTIVELY DISTINGUISH TRANSIENT FROM PERSISTENT SODIUM CHANNELS

(75) Inventors: Joseph S. Adorante, Irvine, CA (US); George R. Ehring, Huntington Beach, CA (US); John Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 406 days.

(21) Appl. No.: 09/989,797

(22) Filed: Nov. 20, 2001

(65) Prior Publication Data

US 2002/0077297 A1    Jun. 20, 2002

Related U.S. Application Data

(60) Provisional application No. 60/252,771, filed on Nov. 22, 2000.

(51) Int. Cl.
*G01N 33/566* (2006.01)
*G01N 27/04* (2006.01)
*C12N 13/00* (2006.01)
*G01R 27/08* (2006.01)
*C12M 1/34* (2006.01)

(52) U.S. Cl. ................ 435/7.2; 435/173.1; 435/173.4; 435/288.7; 324/447; 324/692

(58) Field of Classification Search ................ 435/7.2, 435/173.1, 173.4, 288.7; 324/447, 692
See application file for complete search history.

(56) References Cited

U.S. PATENT DOCUMENTS

| 5,527,814 | A | | 6/1996 | Louvel ........................ 514/367 |
| 5,610,184 | A | | 3/1997 | Shahinian, Jr. .............. 514/540 |
| 5,922,746 | A | | 7/1999 | Adorante ..................... 514/373 |
| 5,981,268 | A | * | 11/1999 | Kovacs et al. ........... 435/287.1 |
| 6,686,193 | B2 | * | 2/2004 | Maher et al. ............ 435/285.2 |

FOREIGN PATENT DOCUMENTS

| EP | 0 608 604 A1 | 10/1993 |
| EP | 0 659 430 A1 | 12/1994 |
| FR | 2714828 | 1/1994 |
| WO | WO 9641166 | * 12/1996 |

OTHER PUBLICATIONS

Gleitz J, Beile A, Peters T. (+/−)-Kavain inhibits veratridine-activated voltage-dependent Na(+)-channels in synaptosomes prepared from rat cerebral cortex. Neuropharmacology. 1995 Sep;34(9):1133-8.*
Bruce R. Ransom et al, Anoxic Injury of Central Myelinated Axons; New York 1993 Raven Press p. 121 through 151.
Role of Na+ Conductance and the Na+-Ca++ Exchanger in Anoxic Injury of CNS White Matter S.G. Waxman, et al Stuttgart 1992 p. 13-31.
Textbook of Ocular Pharmacology New York 1997 p. 330-334.
Charles P. Taylor, "Na+ Currents That Fail to Inactivate", TINS, pp. 455-460. vol. 16, No. 11, 1993.
Jesus E. Gonzalez and Roger Y. Tsien, "Voltage Sensing by Fluorescence Resonance Energy Transfer in Single Cells", Biophysical Journal, Oct. 1995, pp. 1272-1280, vol. 69.
Sheila A. Doggrell and Brett. E. Bishop, "Effects of Potassium Channel Blockers on the Action Potentials and Contractility of the Rat Right Ventricle", Gen. Pharmac., 1996, pp. 379-385, vol. 27, No. 2.
Nhung T. Nguyen and Robert W. Siegler, "Capillary Electrophoresis of Cardiovascular Drugs", Journal of Chromatography A, pp. 123-150, 1996, vol. 735.
Richard M. Eglen, John C. Hunter and Andre Dray, "Ions in the Fire: Recent Ion-Channel Research and Approaches to Pain Theraphy", TIPS, Aug. 1999, pp. 337-342, vol. 20.
Jesus E. Gonzalez, Kahuku Oades, Yan Leychkis, Alec Harootunian and Paul A. Negulescu, "Cell-Based Assays and Instumentation for Screening Ion-Channel Targets", DDT, Sep. 1999, pp. 431-439, vol. 4, No. 9.
Peter K. Stys, et al, Ionic Mechanisms of Anoxic Injury in Mammallian Role ofNa+ Channels and Na+Ca2+ Exchange.
The Extracellular Patch Clamp: A Method for Resolving Currents Through Indivicual Open Channels in Biological Membrances Neher et al 1978.
Improved Patch-Clamp Techniques for High-Resolution Current Recording From Cells and Cell-Free Membrane Patche O.P. Hamill et al Verlag 1981.
Role of Extracellular Calcium in Anoxic Injury of Mammalian Central White Matter Peter K. Stys et al USA 1990.
Arachidonic Acid Inhibits Sodium Currents and Synaptic Transmission in Cultured Straital Neurons, Douglas D. Fraser Cell Press 1993.

(Continued)

*Primary Examiner*—Joseph Murphy
(74) *Attorney, Agent, or Firm*—Dean G. Stathakis; Martin A. Voet; Joel B. German (57) ABSTRACT

A method for identifying a $Na^+$ channel blocker, including providing a cell containing a $Na^+$ channel, demonstrating both a transient and a persistent current. The cell includes a potassium ($K^+$) channel and a Na/K ATPase ($Na^+$ pump). A fluorescent dye is disposed into the well. The fluorescent dye is sensitive to change in cell membrane potential in order to enable optical measurement of cell membrane potential. A $Na^+$ channel blocker, to be identified, is added to the well and a stimulating current is passed through the cell in an amount sufficient to generate an action potential before and after the addition of the $Na^+$ channel blocker. Thereafter, a change in cell membrane potential is optically measured.

36 Claims, 3 Drawing Sheets

OTHER PUBLICATIONS

Protective Effects of Antiarrhythmic Agents Against Anoxic Injury in CNS White Matter Peter K. Stys. Ontario, Canada 1994.

Calcium: Still Center-Stage in Hypoxic-Ischemic Neuronal Death Dennis W. Choi USA 1995 p. 58-60.

Interaction Between Exteral Na+ and Mexilentine on Na+ Channel in Guinea-Pig Ventricular Myoctes, Masahiro Ono Japan 1995 p. 101-109.

Noninactivating, Tetrodtoxin-Sensitive Na+ Conductance in Rat Optic Nerve Axons Peter Stys p. 6976-6980 USA 1993.

* cited by examiner

$g_K = g_{Na}$  $V_m \simeq -40 mv$

FIG. 4.

QUABAIN $g_K >> g_{Na}$ PERSISTENT

Fig. 5.

HIGH-THROUGHPUT SCREEN FOR IDENTIFYING CHANNEL BLOCKERS THAT SELECTIVELY DISTINGUISH TRANSIENT FROM PERSISTENT SODIUM CHANNELS

The present application claims priority from U.S. Ser. No. 60/252,771 filed Nov. 22, 2000.

The present invention generally relates to screens for identifying channel blockers and, and more particularly, relates to a high-throughput screen for identifying channel blockers that selectively distinguish transient from persistent, or non-inactivating, sodium channels.

Voltage-gated sodium ($Na^+$) channels are crucial for electrical activity in nerve, muscle and heart cells. They mediate the upstroke of the action potential. It is the action potential that is responsible for electrical transmission in the nervous system, and contractility in the heart and skeletal muscle (Aidley, 1991). For a recent review of $Na^+$ channel structure and function see Catterall (2000). Generally, under resting conditions $Na^+$ channels are closed until a stimulus depolarizes the cell to a threshold level. At this threshold $Na^+$ channels begin to open and subsequently rapidly generate the upstroke of the action potential. Normally during an action potential $Na^+$ channels open very briefly (one millisecond) and then close (inactivate) until the excitable cell (neuron, myocyte, muscle) repolarizes to its resting potential.

The above described behavior of voltage-gated $Na^+$ channels can be understood as follows. $Na^+$ channels reside in three major conformations or states. The resting or closed state predominates at negative membrane potentials ($\leq -60$ mV). Upon depolarization, the channels enter the active state and open to allow current flow. The transition from resting to active states occurs within a millisecond after depolarization to positive membrane potentials. Finally during sustained depolarizations ($\geq 1-2$ ms), the channels enter a second closed or inactive state. Subsequent re-openings of the channels require a recycling of the channels from the inactive to the resting state, which occurs when the membrane potential returns to negative values. This means that membrane depolarization not only opens sodium channels but also causes them to close even during sustained depolarizations (Hodgkin and Huxley, 1952). Thus normal $Na^+$ channels open briefly during depolarization and are closed at rest ($\leq -60$ mV).

However, some $Na^+$ channels may be open under resting conditions at relatively negative membrane potentials and even during sustained depolarization (Stys, 1998; Taylor, 1993). These non-inactivating $Na^+$ channels generate what is known as a persistent $Na^+$ current, see FIG. 1. Persistent $Na^+$ channels have these properties because they activate (open) at more negative membrane potentials than normal $Na^+$ channels and inactivate at more positive potentials (Alonso et al, 1999). This means that these persistent $Na^+$ channels may be open at membrane potentials as negative as $-80$ mV (Stys, 1998) and stay open at potentials as positive as 0 mV (Alonso, et al, 1999).

The above described unique properties of persistent $Na^+$ channels are exploited in the assays in accordance with the present invention. These persistent $Na^+$ channels are thought to be involved in synaptic amplification and modification of spiking behavior and also in the generation of conditions leading to cellular dysfunction (Ragsdale et al, 1998; and Taylor, 1993).

Besides their importance under physiological conditions, $Na^+$ channels are also important under pathophysiological situations. For example they appear play a role in epileptic seizures, cardiac arrhythmias, and ischemia/hypoxia-induced cardiac and neuronal cell death (Taylor et al, 1997; Ragsdale et al, 1998). Importantly, the persistent $Na^+$ current appears to play a major role in generating the above mentioned cellular abnormalities (Stys, 1998; Taylor et al, 1997). For example persistent $Na^+$ current is upregulated in both cardiac and neuronal cells during hypoxia (Saint et al, 1996; Hammarstrom, 1998) and may ultimately lead to overload of cell $Na^+$ and calcium, conditions leading to cell death (Stys, 1998). Blockers of voltage-gated $Na^+$ channels have been shown to be effective in ameliorating cellular dysfunctions and death resulting from errant operation of voltage-gated sodium channels (Stys, 1998). However, in many cases these blockers inhibit both the normal (transient) and noninactivaing (persistent) $Na^+$ channels to the same extent. Significant block of normal transient $Na^+$ channels could seriously compromise cellular and organ function or may even cause death. Thus assuming that the persistent $Na^+$ current is the therapeutic target, it is important to develop drugs that will block this component of $Na^+$ current but not the normal transient current. However, in order to discern whether a compound selectively blocks the persistent over the transient $Na^+$ current conventional electrophysiological methods such as whole cell patch clamping or voltage clamping in oocyte preparations must be performed (Marty and Neher, 1995; Shih et al, 1998).

Although voltage clamp methods give detailed information about transient and persistent $Na^+$ currents only a relatively few compounds can be tested using these conventional electrophysiological techniques. Drug discovery programs trying to find highly selective blockers of the persistent $Na^+$ current are therefore in need of a rapid high throughput screen that will facilitate the testing of large numbers of compounds simultaneously. Until now no such screen exits.

SUMMARY OF THE INVENTION

A method for identifying a $Na^+$ channel blocker in accordance with the present invention generally includes providing a cell containing a $Na^+$ channel. The channel demonstrate both transient and persistent currents. The cell also includes a potassium $K^+$ channel and a Na/K ATPase ($Na^+$ pump). A fluorescent dye is disposed into the well. The fluorescent dye is sensitive to change in cell membrane potential in order to enable optical measurement of cell membrane potential. A $Na^+$ channel blocker, to be assayed, screened or otherwise identified, is added to the well and a stimulation current is passed through the cell in an amount sufficient to generate an action potential before and after the addition of the $Na^+$ channel blocker. Thereafter, a change in cell membrane potential is optically measured.

Apparatus in accordance with the present invention includes a screen for identifying a $Na^+$ channel blocker. The screen includes at least one cell comprising a $Na^+$ channel, the channel demonstrating both transient and a persistent current. In addition, the cell further comprises a potassium (K) channel and a Na/K ATPase ($Na^+$) pump. At least one well for containing the cell is provided. A fluorescent dye sensitive to change in cell membrane potential in order to enable optical measurement of cell membrane potential is also included. Electrodes disposed in the well are in the well are provided for passing a stimulating current through said cell sufficient to generate an action potential before and after the addition of the $Na^+$ channel blocker, to be identified, to said cell.

BRIEF DESCRIPTION OF THE DRAWINGS

The advantages and features of the present invention will be better understood with the following detailed description when considered in conjunction with the accompanying drawings of which:

FIG. 2 is a representation of a genetically engineered cell, containing sodium channels that exhibit both transient and persistent currents, enabling a depolarization assay. The engineered cell contains K channels (denoted by gK for K conductance), $Na^+$ channels exhibiting normal transient (gNa) and noninactivating/persistent ($gNa_{persistent}$) currents and a $Na^+$ pump that maintains the cellular ion gradients. For optimal sensitivity the K conductance (gK) and persistent $Na^+$ conductance ($gNa_{persistent}$) should be similar (order of magnitude). $gK \approx gNa_{persistent}$. These cells will be plated in wells and suspended in Na-free media. Concentrated KCl is first added to the wells (see text) to induce a small depolarization. This is followed by the addition of NaCl to the wells and will cause a further depolarization as $Na^+$ moves through open persistent $Na^+$ channels;

FIG. 3 is a representation similar to FIG. 2 of a cell enabling a hyperpolarization assay. The engineered cell contains K channels (denoted by gK for K conductance), $Na^+$ channels exhibiting normal transient (gNa) and noninactivating/persistent ($gNa_{persistent}$) currents and a $Na^+$ pump that maintains the cellular ion gradients. In this case $gK=gNa_{persistent}$ (equal conductance). Thus the membrane potential should be near midway the equilibrium (Nernst) potential for $K^+$ ($E_K$) and $Na^+$ ($E_{Na}$). Assuming cell and media $K^+$ and $Na^+$ concentrations of 140 and 20 and 2 and 80 mM respectively $E_K=-107$ mV and $E_{Na}=35$ mV. Thus the resting membrane potential will be near −36 mV. Upon blockage of persistent $Na^+$ channels $E_m$ will hyperpolarize towards $E_K$ (theoretically by as much as 70 mV);

FIG. 4 is a representation of a cell similar to FIGS. 2 and 3 enabling a secondary depolarization following ouabain addition. The engineered cell contains $K^+$ channels (denoted by gK for K conductance), $Na^+$ channels exhibiting normal transient (gNa) and noninactivating/persistent ($gNa_{persistent}$) currents and a $Na^+$ pump that maintains the cellular ion gradients. In this case $gK>>gNa_{persistent}$. Addition of ouabain will result in a small depolarization followed by a much larger secondary depolarization. In the absence of a significant Cl conductance or in Cl-free media $Na^+$ gained via persistent $Na^+$ channels can not be removed by the $Na^+$ pump therefore the cell gains $Na^+$ in exchange for $K^+$. As the cell loses $K^+$, $E_K$ becomes more positive and the cell depolarizes. Blockers of persistent $Na^+$ channels will prevent the secondary depolarization.

DETAILED DESCRIPTION

The present invention uses a genetically engineered cell containing appropriate subtype of $Na^+$ channel, i.e., one that demonstrates both a transient and persistent current. Such a cell can be engineered by incorporating a cDNA for a $Na^+$ channel with the appropriate biophysical properties into cell type that does not normally contain channels of this type. The cDNAs for several families of $Na^+$ channels have been cloned and sequenced (for reviews see Goldin, 1999; Catterall, 2000). These cDNAs may be introduced into cell lines by well known molecular biological methods (Sambrook and Russell, 2000). In addition, cell lines that endogenously express $Na^+$ channels with the appropriate properties can be used and are included in the present invention. The cell may also contain a potassium (K) channel and a Na/K ATPase ($Na^+$ pump). A 96–386 well plate assay system 10 may be used in conjunction an optical system 20 using well known methods to measure membrane potential (see FIG. 5). Fluorescent dyes have been widely used to monitor membrane potential within neuronal and other cell types (Grinvald et al., 1988; Lowe, 1988). The voltage-sensitive dye will be required to have high sensitivity and respond very rapidly to changes in membrane potential such as those generated during an action potential (Gonzalez et al 1995; 1997). A fast ratiometric voltage-sensitive fluorescence dye based on resonance energy transfer (FRET) as described in U.S. Pat. Nos. 5,662,035 and 6,107,066 could be used for such an assay. The actual specifics of the invention will be described below in detail.

Figure 1:
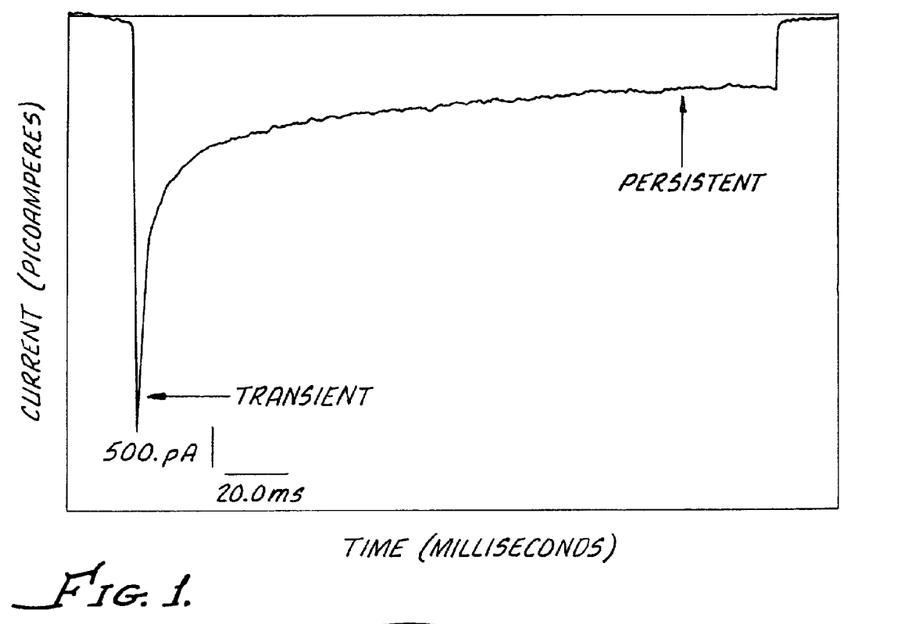
FIG. 1 is a plot of current vs. time for voltage-gated $Na^+$ channels upon sustained depolarization showing a combination of inactivating $Na^+$ channels transient current and non-inactivating $Na^+$ channel persistent current.

With reference to FIG. 1, there is shown is a current record of a HEK-293 cell containing transected Type III $Na^+$ channels. These channels are known to generate both persistent and transient $Na^+$ currents. The cell was patch clamped in the whole cell configuration and depolarized from a holding potential of −80 to −10 mV. The record shows both transient and persistent current components. A rapidly decaying current is followed by a sustained persistent $Na^+$ current as described in the text.

Figure 2:
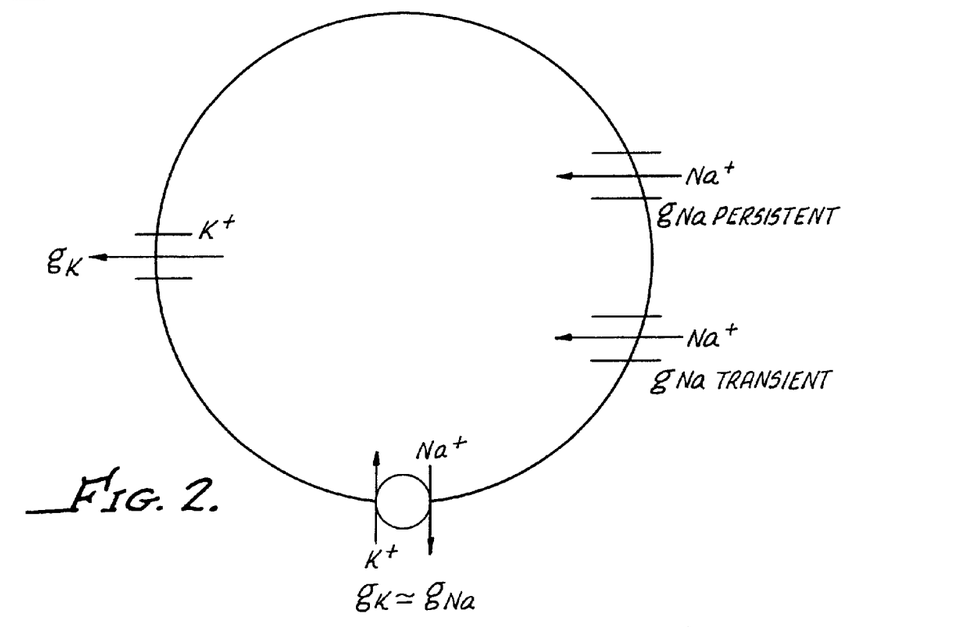

FIG. 2 is a representation of a genetically engineered cell containing sodium channels that exhibit both transient and persistent currents. In addition the cell contains K channels and $Na^+$ pumps. A major requirement of the assay in accordance with the present invention is that the potassium conductance (gK) be of the appropriate magnitude such that addition of K to a bath containing the cell to cause a measurable depolarization. In addition, following activation, the conductance of the persistent component of the $Na^+$ channel ($gNa_{persistent}$) must be large enough to produce a voltage change when extracellular $Na^+$ is introduced into a Na-free assay medium.

To begin the present assay the engineered cells are plated onto the wells 12 of the 96–386 well assay plate 10. The cells are in a Na-free physiological buffer that for example, can contain in mM: 135 NMDG (N-methyl-d-glucamine)Cl, 5 KCl, 2.0 $CaCl_2$, 1.5 mM $MgCl_2$ and 20 mM Hepes pH adjusted to 7.4. The first addition to the wells will be a concentrated stock of KCl to elevate the $K^+$ concentration enough to induce a small (10 mV or more) depolarization thus activating $Na^+$ channels. However, in the absence of extracellular $Na^+$ no additional depolarization will be seen. Within a few milliseconds following $K^+$ addition the transient $Na^+$ channels will activate and then inactivate yet the channels generating the persistent $Na^+$ current will remain open.

Since there is no extracellular $Na^+$ ($NMDG^+$ substitutes for Na) and NMDG does not permeate $Na^+$ channels no depolarization will occur. However, following addition of a concentrated stock of NaCl to the wells, the open $Na^+$ channels that generate the persistent current should cause the membrane to depolarize. The magnitude of the depolarization will depend on the concentration of $Na^+$ added to the bath and the relative conductance of the $Na^+$ channels generating the persistent current. The larger the depolarization the easier it will be to perform reliable dose responses with compounds of interest.

The present assay therefore allows one to discover compounds that block the persistent $Na^+$ current and as such is a screen for persistent $Na^+$ channels. However, the assay does not address whether compounds that are found to block persistent $Na^+$ channels also block $Na^+$ channels generating the transient current. As will be hereinafter described how a parallel assay will discern whether compounds found to block persistent sodium current in the above described assay also block transient $Na^+$ current generated by typical $Na^+$ channels.

Figure 3:
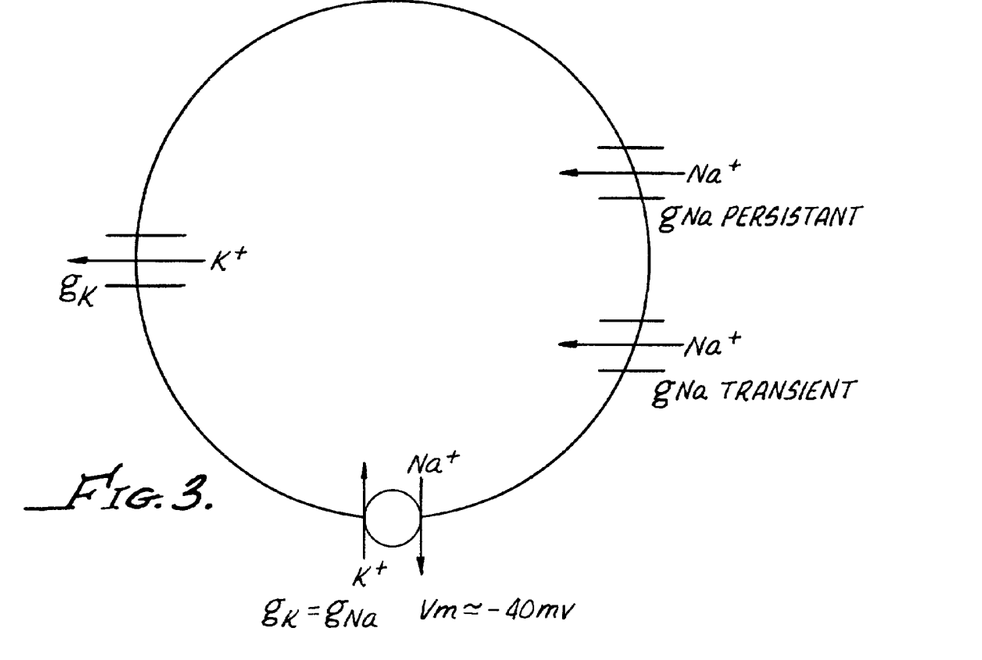

FIG. 3 is a variation of the cell represented in FIG. 2 to be used to screen blockers of persistent $Na^+$ channels. This assay takes advantage of the fact that persistent $Na^+$ channels are open at relatively negative membrane potentials as described previously (Stys, 1998). In this case the cell is engineered with $K^+$ and $Na^+$ channels such that the relative conductance of the $K^+$ channel and the portion of the $Na^+$ channels generating the persistent current are very similar. This will make the resting membrane potential lie approximately halfway between the equilibrium potential (Nernst) potential for $Na^+$ and that of $K^+$ (–40 to –20 mV). Under these conditions noninactivaing $Na^+$ channels remain open and depolarize the cell membrane. Thus, blocking the noninactivating $Na^+$ channels will hyperpolarize the membrane towards the equilibrium potential for $K^+$. Total block of persistent $Na^+$ channels could result in a significant hyperpolarization, as much as 50 to 60 mV (depending on the equilibrium potentials for $Na^+$ and $K^+$. In this case only one addition need be made and concerns about changes in cell volume due to changes in osmolarity (no concentrated stocks of KCl or NaCl will be added) are of no consequence since drug concentrations will be in the micromolar range. This screen should allow detection of agents that block persistent $Na^+$ current generated by noninactivating $Na^+$ channels.

Figure 4:
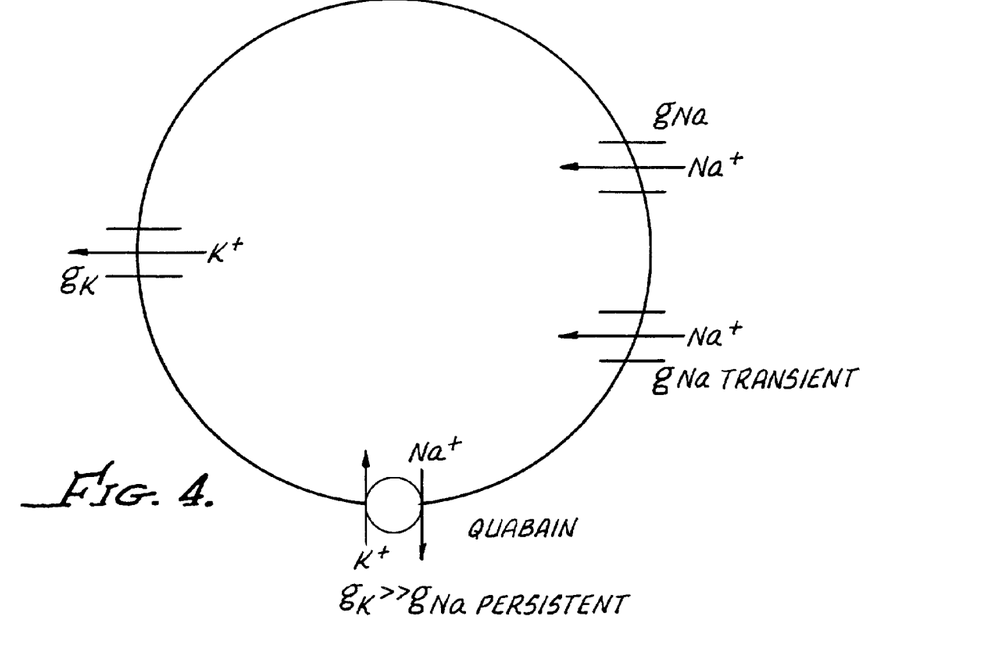

FIG. 4 shows a variation of a cell for detecting blockers of persistent $Na^+$ channels in a high throughput screen. In this engineered cell there are $K^+$ channels, voltage gated $Na^+$ channels, containing a portion whose current is persistent, and a ouabain-sensitive Na/K ATPase ($Na^+$ pump). In this case $gK>>gNa_{persistent}$. This means that the resting membrane potential will be near $E_K$.

To start the assay, ouabain is added to the bath in order to block the $Na^+$ pump. This will lead to a small depolarization (due to blockage of the electrogenic $Na^+$ pump) and a large secondary depolarization. This secondary depolarization is the key to the assay and relies on the fact that the equilibrium potential for $K^+$ will become more positive. The rationale is as follows. Following ouabain addition, the cell will gain $Na^+$ via persistent $Na^+$ channels that are open at near resting membrane potential. In the absence of a Cl conductance (or in a $Cl^-$ free medium) the $Na^+$ gained by the cell will be electrically compensated for by an equimolar loss of $K^+$. Since the relative gK is large millimolar loss $K^+$ will result in a depolarization as its Nernst potential becomes more positive. The extent of the depolarization will depend on the amount of $Na^+$ gained and thus $K^+$ lost by the cell following the addition of ouabain. Compounds that block the persistent $Na^+$ channels will prevent this depolarization and do so in a dose-dependent manner.

Any of the above methods will allow identification of compounds that inhibit noninactivating/persistent $Na^+$ channels. However, it is possible that these compounds may also block the channels generating transient $Na^+$ currents. Thus the second part of the screen in accordance with the present invention addresses how compounds that preferentially block persistent but not transient $Na^+$ channels can be distinguished.

Figure 5:
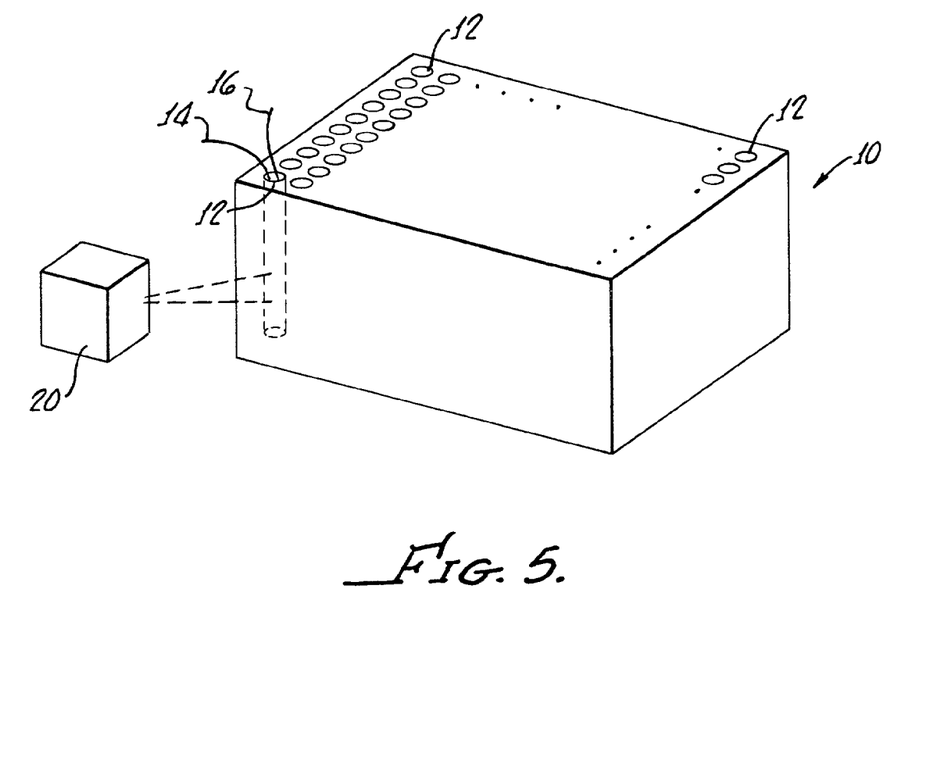
FIG. 5 is a representation of a 96–386 well plate suitable for use in the present invention showing a pair of electrodes disposed in each well.

With reference to FIG. 5 a well plate 10 includes wells 12 each containing a pair of silver/silver chloride or platinum electrodes 14, 16 in order to pass a stimulating current sufficient in magnitude to generate an action potential in the engineered cells discussed previously. The use of a fast voltage sensitive dye (FRET) as described above, enables an optical system 20 to measure membrane potential. Using this current passing method, (field stimulation), action potentials may be generated at will before and after the presence of a $Na^+$ channel blocker shown to inhibit persistent $Na^+$ channels. A dose response may then be performed to observe if the drug in question blocks the action potential and therefore a significant portion of the transient $Na^+$ current. In this way drugs that preferentially block persistent transient $Na^+$ channels may be discovered in a rapid high throughput format.

Specific $Na^+$ channels blockers like TTX that do not discriminate very well between transient and persistent $Na^+$ channels are expected to inhibit both channels to nearly the same extent. On the other hand it should be observed that drugs such as lidocaine and mexilitine block persistent $Na^+$ currents/channels at concentrations that have no effect on transient $Na^+$ channels and therefore have no effect on action potentials.

These assays can be performed using robotic systems (not shown) that are frequently used for high throughput screens in the pharmaceutical industry. The chances for discovering novel compounds that block or modify persistent $Na^+$ currents while sparing transient $Na^+$ currents should be measurably increased. Compounds that are selected by the above screens may then be examined in great detail using conventional electrophysiological methods for further examination and ultimate selection of a lead structure.

REFERENCES

All of the following references are to be incorporated into the present application for the purpose of further describing certain procedures and properties set forth in this application which are well known in the art.

Aidley, D. J. (1991). The Physiology of Excitable Cells. Third Edition. Cambridge University Press.

Catterall, W A. (2000). From ionic currents to molecular mechanisms: The structure and function of voltage-gated sodium channels. Neuron, 26: p 13–25.

Goldin, A. L. (1999). Diversity of mammalian voltage-gated sodium channels. Ann N Y Acad Sci., 868:38–50

Gonzalez, J. and Tsien R. (1997). Improved indicators of cell membrane potential that use fluorescence resonance energy transfer. Chemistry and Biology 4: p269–277.

Gonzalez, J. and Tsien R. (1995). Voltage sensing by fluorescence resonance energy transfer in single cells. Biophysical Journal 69: p 1272–1280.

Hammarstrom, A. K. M. and Gage, P. W. (1998). Inhibition of oxidative metabolism increases persistent sodium current in rat CA1 hippocampal neurons. Journal of Physiology 510.3: p 735–741.

Hodgkin, A. L. and Huxley, A. F. (1952). A quantitative description of membrane current and its application to conduction and excitation in nerve. The Journal of Physiology 117: p500–544.

Ju, Y. K., Saint, D. A. and Gage, P. W. (1996). Hypoxia increases persistent current in rat ventricular myocytes. Journal of Physiology 497.2: p 337–347.

Magistretti, J. and Alonso, A. (1999). Biophysical properties and slow voltage-dependent inactivation of sustained sodium current in entorhinal cortex layer II principle neurons. A whole cell and single channel study. Journal of General Physiology 114: p491–509.

Sambrook, J. and Russell D. (2000) Molecular cloning—A laboratory manual, $3^{rd}$ ed., Cold Spring Harbor Press, Cold Spring Harbor, N.Y.

Marty, A. and Neher, E. (1995). Tight-seal Whole-cell recording. In: *Single Channel Recording*. Sakmann, B., and Neher, E. Editors. 1995. Plunem Press, New York.

Ragsdale, D. S. and Avoli, M. (1998). Sodium channels as molecular targets for antiepileptic drugs. Brain Research Reviews 26: p 16–28.

Shih, T. M., Smith, R. D., Toro, L., and Goldin, A. L. (1998). High level expression and detection of ion channels in Xenopus oocytes. Methods in Enzymology 293: p529–556.

Stys, P. (1998). Anoxic and ischemic injury of myelinated axons in the CNS white matter: From mechanistic concepts to therapeutics. Journal of Cerebral Blood Flow and Metabolism. 18: p 2–25.

Taylor, C. P. (1996). Voltage-gated sodium channels as targets for anticonvulsant, analgesic, and neuroprotective drugs. Current Pharmaceutical Design 2: p 375–388.

Taylor, C. P. and Narasimhan, L. S. (1997). Sodium Channels and Therapy of Central Nervous System Diseases. Advances in Pharmacology 39: p 47–98.

Taylor, C. P. (1993). $Na^+$ currents that fail to inactivate. Trends in Neuroscience 16: p 455–460.

Although there has been hereinabove described a method and screen for identifying a $Na^+$ channel blocker, in accordance with the present invention, for the purposes of illustrating the manner in which the invention may be used to advantage, it will be appreciated that the invention is not limited thereto. Accordingly, any and all modification, variations or equivalent arrangements which may occur to those skilled in the art should be considered to be within the scope of the invention as defined in the appended claims.

What is claimed is:

1. A method for identifying a selective blocker of a persistent $Na^+$ channel whereby the method comprises the steps of:
   a) providing a test sample 1 comprising
      i) a $Na^+$-free physiological buffer;
      ii) a voltage-sensitive fluorescence dye;
      iii) a cell having a $K^+$ channel, a transient $Na^+$ channel and a persistent $Na^+$ channel; and
      iv) a potential $Na^+$ channel blocker;
   b) depolarizing membrane of the cell in the test sample 1;
   c) generating a current through the persistent Na+ channel by adding $Na^+$ to test sample 1 at least 10 msec after step (b);
   d) detecting fluorescence emitted by the voltage-sensitive dye in test sample 1;
   e) providing a control sample 1 comprising
      i) a $Na^+$-free physiological buffer;
      ii) a voltage-sensitive fluorescence dye; and
      iii) a cell having a $K^+$ channel, a transient $Na^+$ channel and a persistent $Na^+$ channel;
   f) depolarizing membrane of the cell in the control sample 1;
   g) generating a current through the persistent $Na^+$ channel by adding $Na^+$ ions to the control sample 1 at least 10 msec after step (f);
   h) detecting fluorescence emitted by the voltage-sensitive dye in the control sample 1;
   i) determining the relative emitted fluorescence 1 by comparing the emitted fluorescence from step (d) to the emitted fluorescence from step (h);
   j) providing a test sample 2 comprising
      i) a physiological buffer;
      ii) a voltage-sensitive fluorescence dye;
      iii) a cell having a $K^+$ channel and a transient $Na^+$ channel; and
      iv) a potential $Na^+$ channel blocker
   k) depolarizing membrane of the cell in test sample 2;
   l) detecting the fluorescence emitted by the voltage-sensitive dye in test sample 2;
   m) providing a control sample 2 comprising
      i) a physiological buffer;
      ii) a voltage-sensitive fluorescence dye; and
      iii) a cell having a $K^+$ channel and a transient $Na^+$ channel;
   n) depolarizing membrane of the cell in control sample 2;
   o) detecting the fluorescence emitted by the voltage-sensitive dye in control sample 2;
   p) determining a relative emitted fluorescence 2 by comparing the emitted fluorescence from step (l) to the emitted fluorescence from step (o);
   q) comparing the relative emitted fluorescence 1 in step (i) with the relative emitted fluorescence 2 in step (p).

2. The method according to claim 1, wherein the cell expresses an endogenous persistent $Na^+$ channel.

3. The method according to claim 1, wherein the cell expresses an exogenous persistent $Na^+$ channel.

4. The method according to claim 3, wherein the cell is HEK-293.

5. The method according to claim 1, wherein the cell expresses a Type III persistent $Na^+$ channel.

6. The method according to claim 1, wherein the membrane depolarization of step (b) is by $K^+$ addition.

7. The method according to claim 1, wherein the membrane depolarization of step (f) is by $K^+$ addition.

8. The method according to claim 1, wherein the membrane depolarization of step (b) and step (f) is by $K^+$ addition.

9. The method according to claim 1, wherein the membrane depolarization of step (b) is by field stimulation.

10. The method according to claim 1, wherein the membrane depolarization of step (f) is by field stimulation.

11. The method according to claim 1, wherein the membrane depolarization of step (b) and step (f) is by field stimulation.

12. The method according to claim 1, wherein the membrane depolarization of step (k) is by field stimulation.

13. The method according to claim 1, wherein the membrane depolarization of step (n) is by field stimulation.

14. The method according to claim 1, wherein the membrane depolarization of step (k) and step (n) is by field stimulation.

15. A method for identifying a blocker of a persistent $Na^+$ channel whereby the method comprises the steps of:
   a) providing a test sample 1 comprising
      i) a $Na^+$-free physiological buffer;
      ii) a voltage-sensitive fluorescence dye;
      iii) a cell having a $K^+$ channel, a transient $Na^+$ channel and a persistent $Na^+$ channel; and
      iv) a potential $Na^+$ channel blocker;

b) depolarizing membrane of the cell in the test sample 1;

c) generating a current through the persistent Na+ channel by adding Na$^+$ to test sample 1 at least 10 msec after step (b);

d) detecting fluorescence emitted by the voltage-sensitive dye in test sample 1;

e) providing a control sample 1 comprising
   i) a Na$^+$-free physiological buffer;
   ii) a voltage-sensitive fluorescence dye; and
   iii) a cell having a K$^+$ channel, a transient Na$^+$ channel and a persistent Na$^+$ channel;

f) depolarizing membrane of the cell in the control sample 1;

g) generating a current through the persistent Na$^+$ channel by adding Na$^+$ ions to the control sample 1 at least 10 msec after step (f);

h) detecting fluorescence emitted by the voltage-sensitive dye in the control sample 1;

i) comparing the emitted fluorescence from step (d) to the emitted fluorescence from step (h).

16. The method according to claim 15, wherein the cell expresses an endogenous persistent Na$^+$ channel.

17. The method according to claim 15, wherein the cell expresses an exogenous persistent Na$^+$ channel.

18. The method according to claim 17, wherein the cell is HEK-293.

19. The method according to claim 15, wherein the cell expresses a Type III persistent Na$^+$ channel.

20. The method according to claim 15, wherein the membrane depolarization of step (b) is by K$^+$ addition.

21. The method according to claim 15, wherein the membrane depolarization of step (f) is by K$^+$ addition.

22. The method according to claim 15, wherein the membrane depolarization of step (b) and step (f) is by K$^+$ addition.

23. The method according to claim 15, wherein the membrane depolarization of step (b) is by field stimulation.

24. The method according to claim 15, wherein the membrane depolarization of step (f) is by field stimulation.

25. The method according to claim 15, wherein the membrane depolarization of step (b) and step (f) is by field stimulation.

26. A method for identifying a selective blocker of a persistent Na$^+$ channel whereby the method comprises the steps of:
   a) providing a test sample 1 comprising
      i) a physiological buffer;
      ii) a voltage-sensitive fluorescence dye; and
      iii) a cell having a K$^+$ channel and a persistent Na$^+$ channel wherein a resting membrane potential of the cell is approximately halfway between an equilibrium potential of Na$^+$ and an equilibrium potential of K$^+$;
   b) detecting fluorescence emitted by the voltage-sensitive dye in test sample 1;
   c) adding a potential Na$^+$ channel blocker to test sample 1;
   d) detecting fluorescence emitted by the voltage-sensitive dye in the test sample 1;
   e) determining a relative emitted fluorescence 1 by comparing the emitted fluorescence from step (b) with the emitted fluorescence from step (d);
   f) providing a test sample 2 comprising
      i) a physiological buffer;
      ii) a voltage-sensitive fluorescence dye;
      iii) a cell having a K$^+$ channel and a transient Na$^+$ channel; and
      iv) a potential Na$^+$ channel blocker
   g) depolarizing membrane of the cell in test sample 2;
   h) detecting the fluorescence emitted by the voltage-sensitive dye in test sample 2;
   i) providing a control sample 2 comprising
      i) a physiological buffer;
      ii) a voltage-sensitive fluorescence dye; and
      iii) a cell having a K$^+$ channel and a transient Na$^+$ channel;
   j) depolarizing membrane of the cell in control sample 2;
   k) detecting the fluorescence emitted by the voltage-sensitive dye in control sample 2;
   l) determining a relative emitted fluorescence 2 by comparing the emitted fluorescence from step (h) relative to an emitted fluorescence from step (k);
   m) comparing the relative emitted fluorescence in step (e) with the relative emitted fluorescence in step (l).

27. The method according to claim 26, wherein the resting membrane potential of the cell is between −40 mV and −20 mV.

28. The method according to claim 26, wherein the membrane depolarization of step (g) is by field stimulation.

29. The method according to claim 26, wherein the membrane depolarization of step (j) is by field stimulation.

30. The method according to claim 26, wherein the membrane depolarization of step (g) and step (j) is by field stimulation.

31. A method for identifying a blocker of a persistent Na$^+$ channel whereby the method comprises the steps of:
   a) providing a test sample 1 comprising
      i) a physiological buffer;
      ii) a voltage-sensitive fluorescence dye; and
      iii) a cell having a K$^+$ channel and a persistent Na$^+$ channel wherein a resting membrane potential of the cell is approximately halfway between an equilibrium potential of Na$^+$ and an equilibrium potential of K$^+$;
   b) detecting fluorescence emitted by the voltage-sensitive dye in test sample 1;
   c) adding a potential Na$^+$ channel blocker to test sample 1;
   d) detecting fluorescence emitted by the voltage-sensitive dye in the control sample 1;
   e) comparing the emitted fluorescence from step (b) with the emitted fluorescence from step (d).

32. The method according to claim 31, wherein the resting membrane potential of the cell is between −40 mV and −20 mV.

33. A method for identifying a selective blocker of a persistent Na$^+$ channel whereby the method comprises the steps of:
   a) providing a test sample 1 comprising
      i) a Cl$^-$-free physiological buffer;
      ii) a voltage-sensitive fluorescence dye;
      iii) a cell having a K$^+$ channel and a persistent Na$^+$ channel wherein a K$^+$ conductance of the K$^+$ channel is at least 50-fold higher than a Na$^+$ conductance from the persistent Na$^+$ channel; and
      iv) a potential Na$^+$ channel blocker;
   b) depolarizing membrane of the cell with a Na/K pump blocker to the test sample 1;
   c) detecting fluorescence emitted by the voltage-sensitive dye in test sample 1;

d) providing a control sample 1 comprising
   i) a Cl⁻-free physiological buffer;
   ii) a voltage-sensitive fluorescence dye; and
   iii) a cell having a K⁺ channel and a persistent Na⁺ channel wherein a K⁺ conductance of the K⁺ channel is at least 50-fold higher than a Na⁺ conductance from the persistent Na⁺ channel;
e) depolarizing membrane of the cell with a Na/K pump blocker to the control sample 1;
f) detecting fluorescence emitted by the voltage-sensitive dye in the control sample 1;
g) comparing the emitted fluorescence from step (c) to the emitted fluorescence from step (f);
h) providing a test sample 2 comprising
   i) a physiological buffer;
   ii) a voltage-sensitive fluorescence dye;
   iii) a cell having a K⁺ channel and a transient Na⁺ channel; and
   iv) a potential Na⁺ channel blocker
i) depolarizing membrane of the cell in test sample 2;
j) detecting the fluorescence emitted by the voltage-sensitive dye in test sample 2;
k) providing a control sample 2 comprising
   i) a physiological buffer;
   ii) a voltage-sensitive fluorescence dye; and
   iii) a cell having a K⁺ channel and a transient Na⁺ channel;
l) depolarizing membrane of the cell in control sample 2;
m) detecting the fluorescence emitted by the voltage-sensitive dye in control sample 2;
n) comparing the emitted fluorescence from step (j) relative to an emitted fluorescence from step (m);
o) comparing the difference in step (g) with the difference in step (n).

34. The method according to claim 33, wherein the Na/K pump blocker is ouabain.

35. A method for identifying a blocker of a persistent Na⁺ channel whereby the method comprises the steps of:
a) providing a test sample 1 comprising
   i) a Cl⁻-free physiological buffer;
   ii) a voltage-sensitive fluorescence dye;
   iii) a cell having a K⁺ channel and a persistent Na⁺ channel wherein a conductance of the K⁺ channel is at least 50-fold higher than a Na⁺ conductance from the persistent Na⁺ channel; and
   iv) a potential Na⁺ channel blocker;
b) depolarizing membrane of the cell with a Na/K pump blocker to the test sample 1;
c) detecting fluorescence emitted by the voltage-sensitive dye in test sample 1;
d) providing a control sample 1 comprising
   i) a Cl⁻-free physiological buffer;
   ii) a voltage-sensitive fluorescence dye; and
   iii) a cell having a K⁺ channel and a persistent Na⁺ channel wherein a K⁺ conductance of the K⁺ channel is at least 50-fold higher than a Na⁺ conductance from the persistent Na⁺ channel;
e) depolarizing membrane of the cell with a Na/K pump blocker to the control sample 1;
f) detecting fluorescence emitted by the voltage-sensitive dye in the control sample 1;
g) comparing the emitted fluorescence from step (c) relative to the emitted fluorescence from step (f).

36. The method according to claim 35, wherein the Na/K pump blocker is ouabain.

* * * * *